(12) United States Patent
Makino et al.

(10) Patent No.: US 10,684,298 B2
(45) Date of Patent: Jun. 16, 2020

(54) AUTOMATED ANALYZER

(71) Applicant: HITACHI HIGH-TECH CORPORATION, Minato-ku, Tokyo (JP)

(72) Inventors: Akihisa Makino, Tokyo (JP); Toshiyuki Inabe, Tokyo (JP); Chie Yabutani, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 58 days.

(21) Appl. No.: 15/758,993

(22) PCT Filed: Jul. 25, 2016

(86) PCT No.: PCT/JP2016/071657
§ 371 (c)(1),
(2) Date: Mar. 9, 2018

(87) PCT Pub. No.: WO2017/043196
PCT Pub. Date: Mar. 16, 2017

(65) Prior Publication Data
US 2019/0339295 A1     Nov. 7, 2019

(30) Foreign Application Priority Data

Sep. 11, 2015 (JP) .................................. 2015-179052

(51) Int. Cl.
*G01N 1/00* (2006.01)
*G01N 35/00* (2006.01)
(Continued)

(52) U.S. Cl.
CPC ........ *G01N 35/0095* (2013.01); *B01L 3/5085* (2013.01); *G01N 33/86* (2013.01);
(Continued)

(58) Field of Classification Search
CPC ........................................................ G01N 1/00
See application file for complete search history.

(56) References Cited

U.S. PATENT DOCUMENTS 6,261,521 B1   7/2001   Mimura et al.
6,594,537 B1   7/2003   Bernstein et al.
(Continued)

FOREIGN PATENT DOCUMENTS

EP   1248170 A1   10/2002
EP   2075583 A2   7/2009
(Continued)

OTHER PUBLICATIONS

European Search Report dated Apr. 18, 2019 for EP Application No. 16 844 060.0.

*Primary Examiner* — Jyoti Nagpaul
(74) *Attorney, Agent, or Firm* — Miles & Stockbridge, P.C.

(57) ABSTRACT

In blood coagulation time measurement, the reaction time relies on the blood coagulation ability of a specimen and is not fixed. In particular, in module-type devices, errors may occur in the specimen processing, measurement number, and measurement time between a plurality of blood coagulation analysis units, leading to the risk of lowering the processing capability of the device as a whole. The present invention is a module-type automated analyzer provided with a plurality of blood coagulation analysis units capable of analyzing blood coagulation time items in which the reaction time between a specimen and a reagent differs depending on the specimen, wherein a control unit that controls the specimen rack conveying operation finds the total of forecasted measurement times of measurement items requested for specimens being analyzed and queued specimens in each of the plurality of blood coagulation analysis units, and determines the conveyance destination of the specimen rack on the basis of the total of the forecasted measurement times that was found.

12 Claims, 11 Drawing Sheets

(51) Int. Cl.
   *B01L 3/00*           (2006.01)
   *G01N 33/86*       (2006.01)
   *G01N 35/04*        (2006.01)

(52) U.S. Cl.
   CPC ....... *G01N 35/00732* (2013.01); *G01N 35/04* (2013.01); *G01N 2035/0097* (2013.01); *G01N 2035/0453* (2013.01)

(56) References Cited

U.S. PATENT DOCUMENTS

| | | |
|---|---|---|
| 9,097,689 B2 | 8/2015 | Yamato et al. |
| 2010/0093097 A1* | 4/2010 | Kawamura ...... G01N 35/00663 436/43 |
| 2010/0101339 A1 | 4/2010 | Tatsutani et al. |
| 2011/0160899 A1 | 6/2011 | Tatsutani et al. |
| 2014/0170023 A1 | 6/2014 | Saito et al. |

FOREIGN PATENT DOCUMENTS

| | | |
|---|---|---|
| JP | 07-092171 A | 4/1995 |
| JP | 10-339734 A | 12/1998 |
| JP | 2001-004639 A | 1/2001 |
| JP | 2003279582 A | 10/2003 |
| JP | 2010-133917 A | 6/2010 |
| JP | 2010-217114 A | 9/2010 |
| JP | 2011-137680 A | 7/2011 |
| WO | WO 2013/035418 A1 | 3/2013 |
| WO | WO 2015/093166 A1 | 6/2015 |

\* cited by examiner

[Fig. 1]
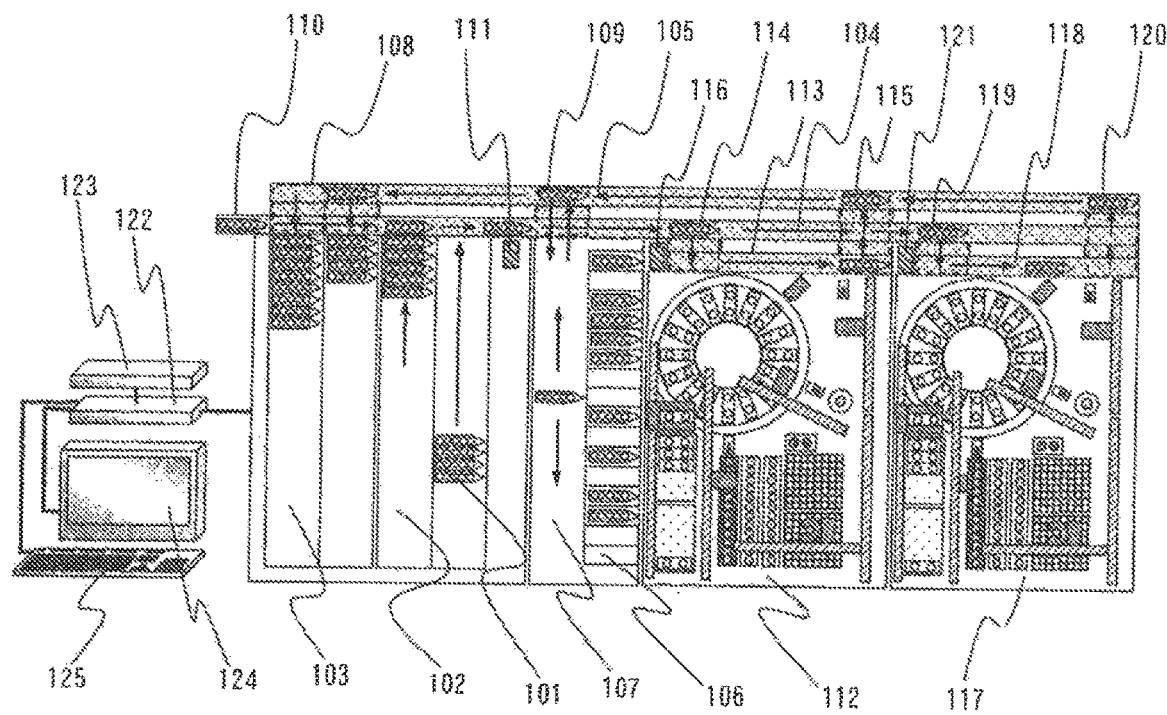
[Fig. 2]
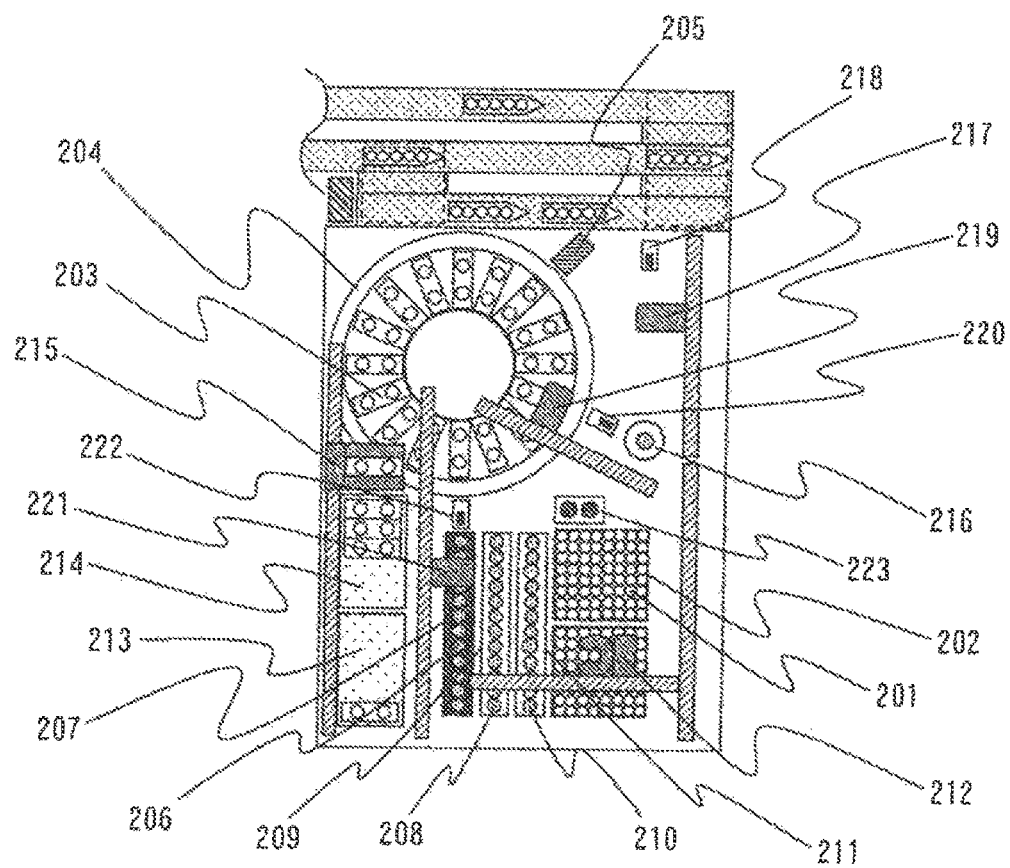

[Fig. 3]

[Fig. 4]
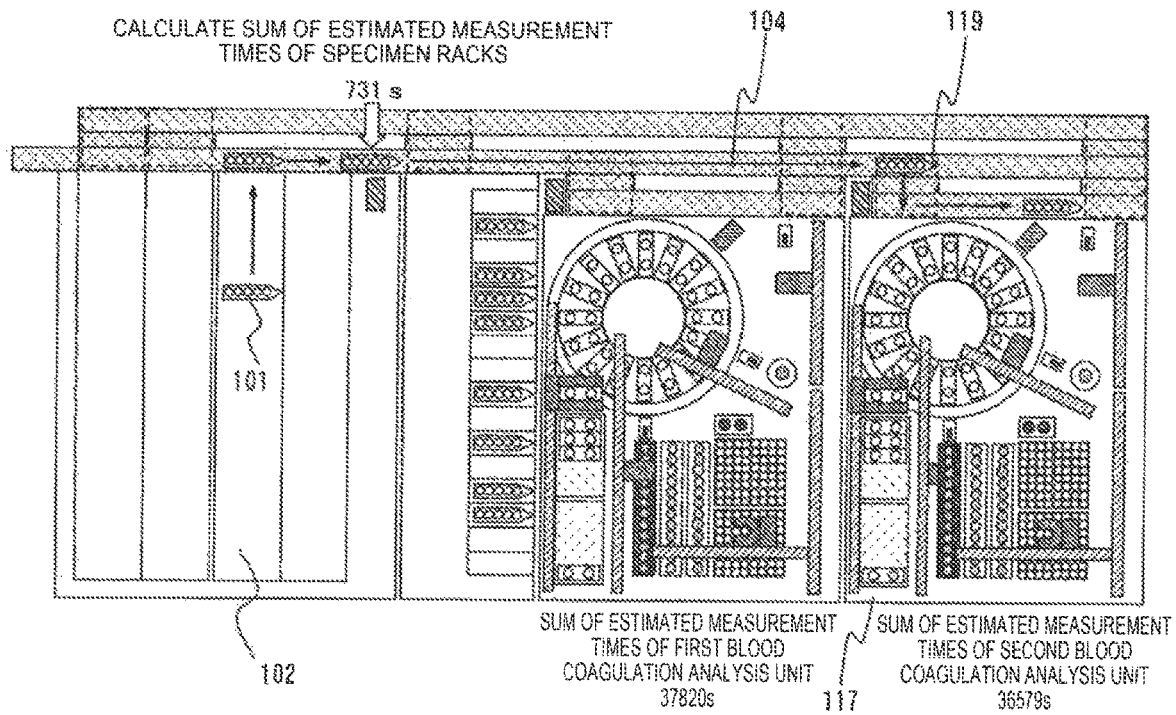
[Fig. 5]
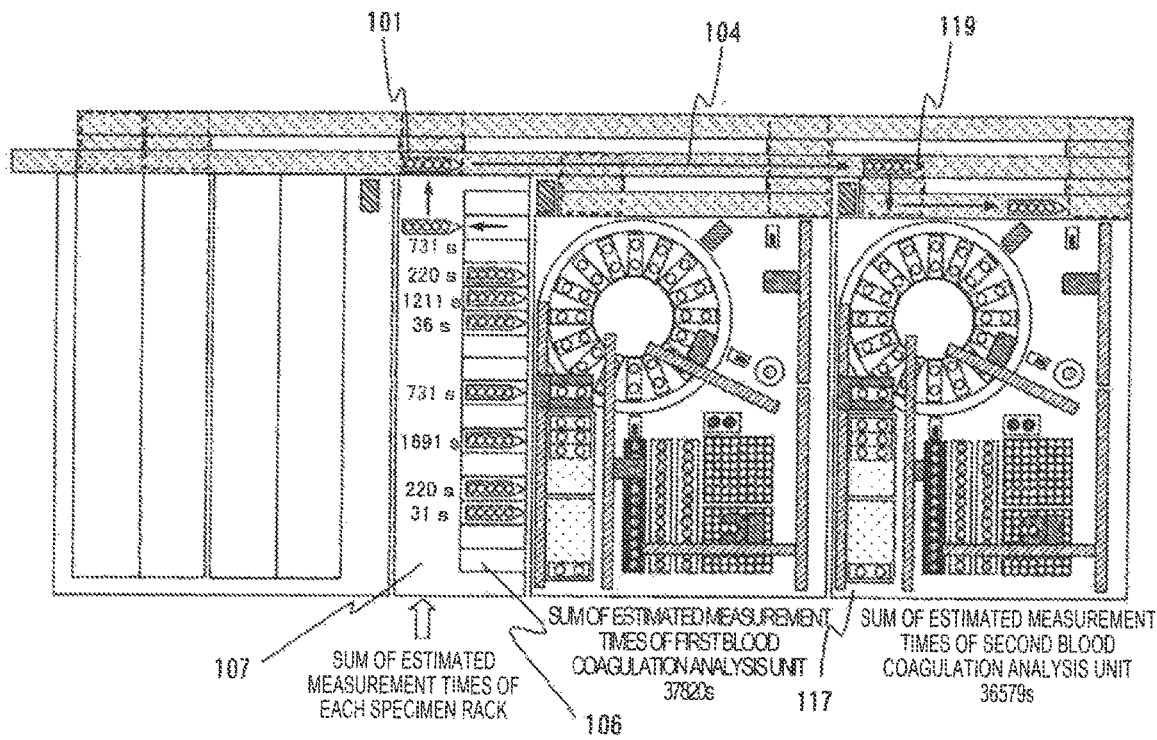

[Fig. 6]
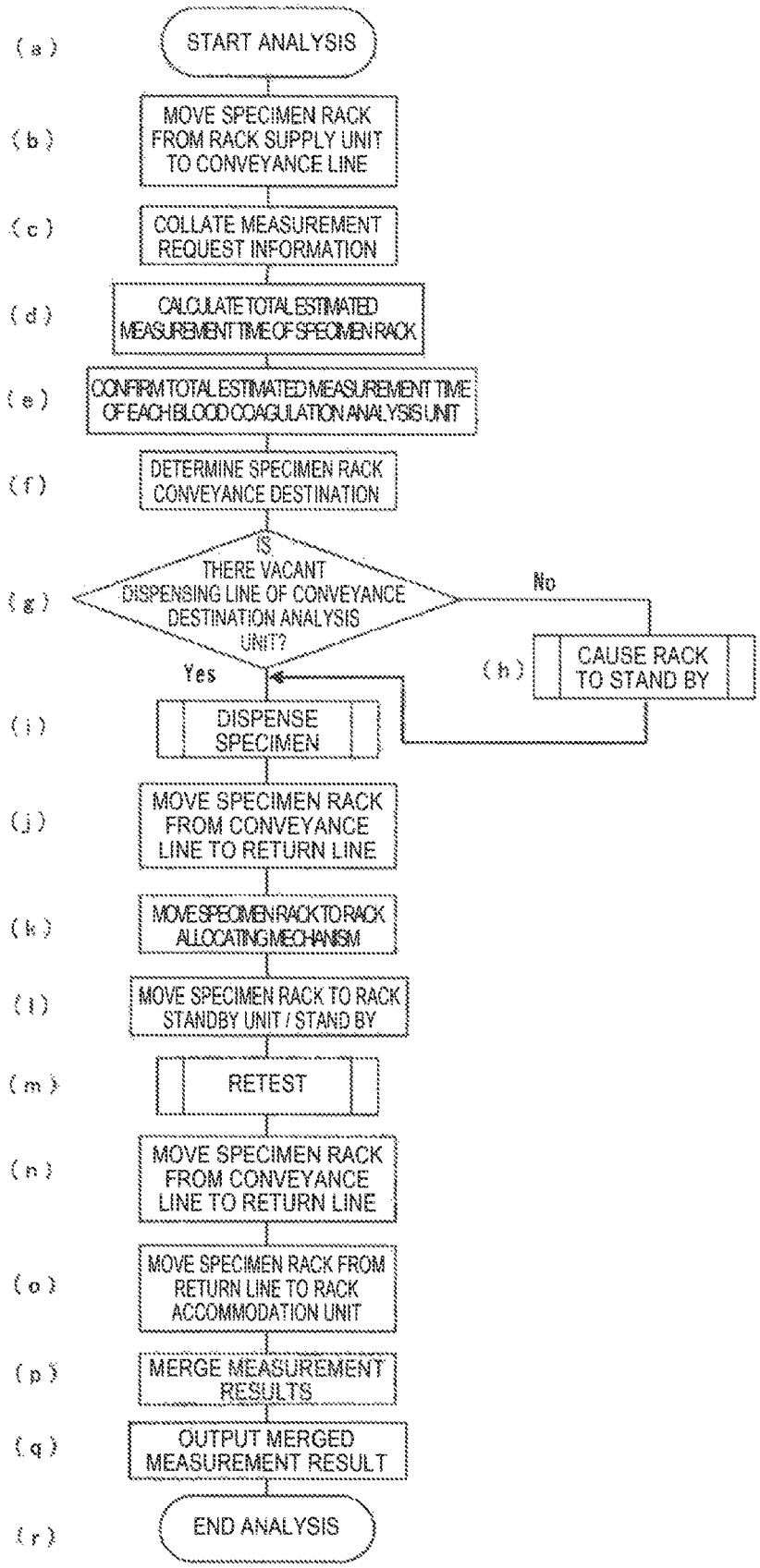

[Fig. 7]
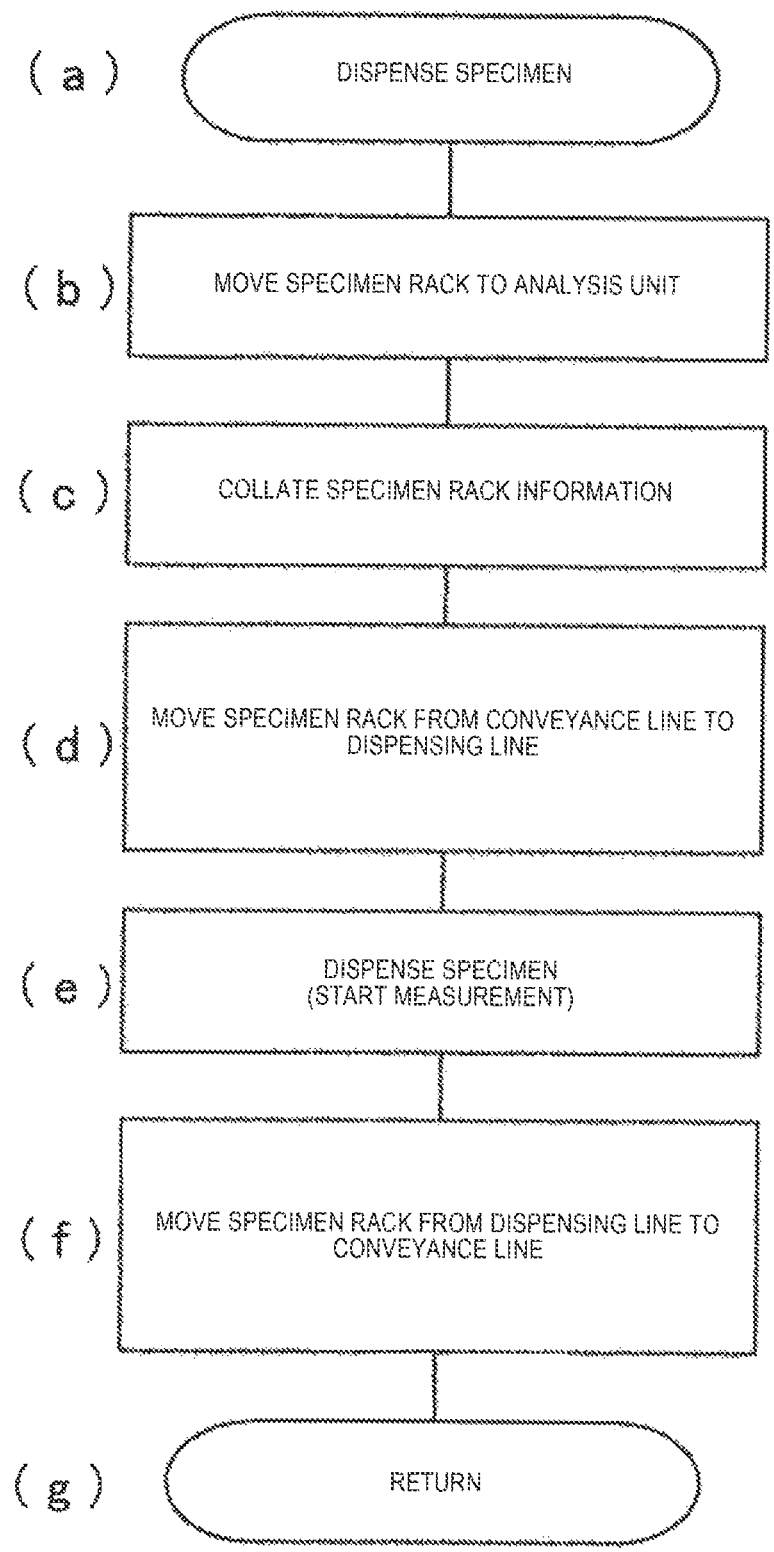

[Fig. 8]
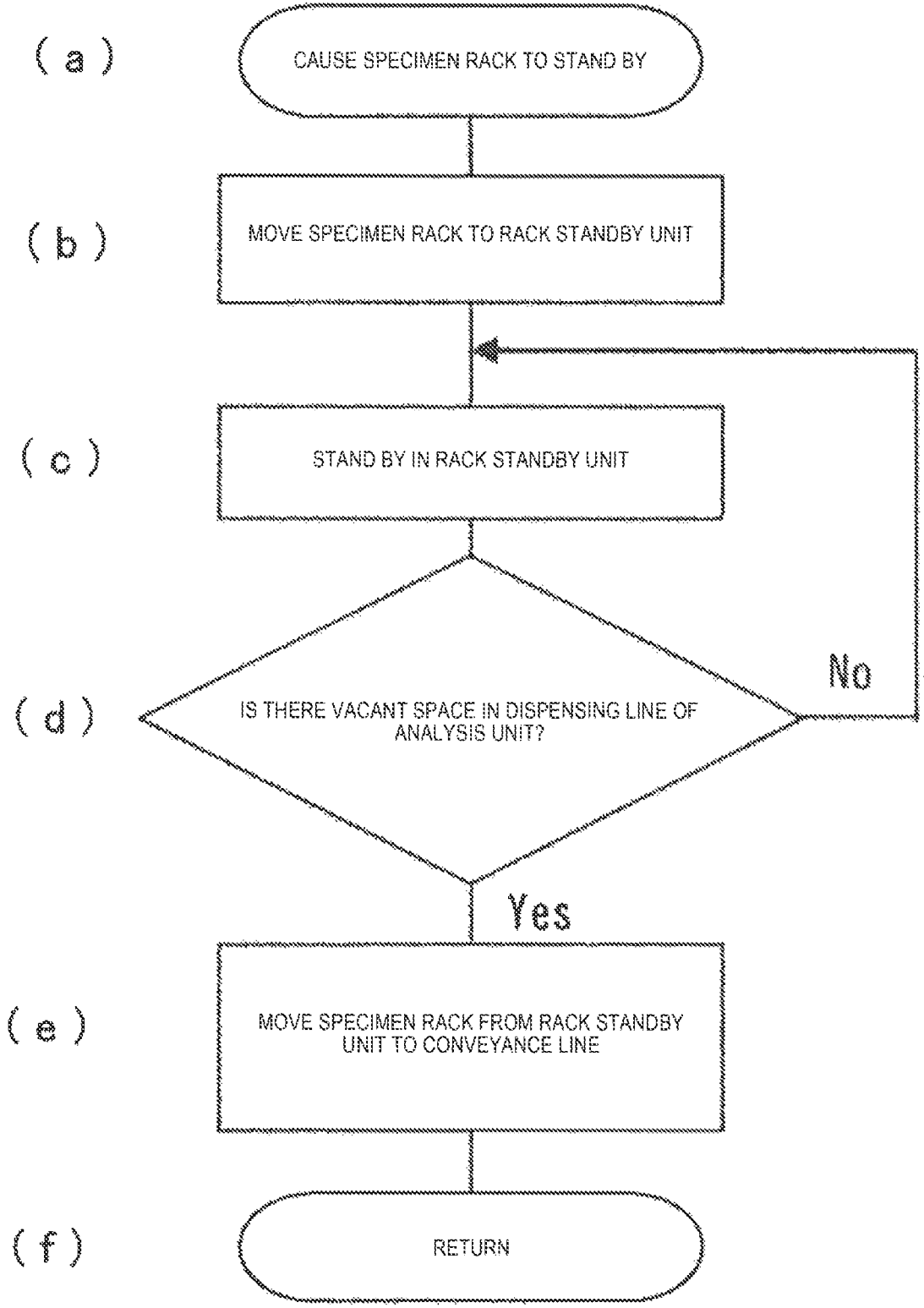

[Fig. 9]
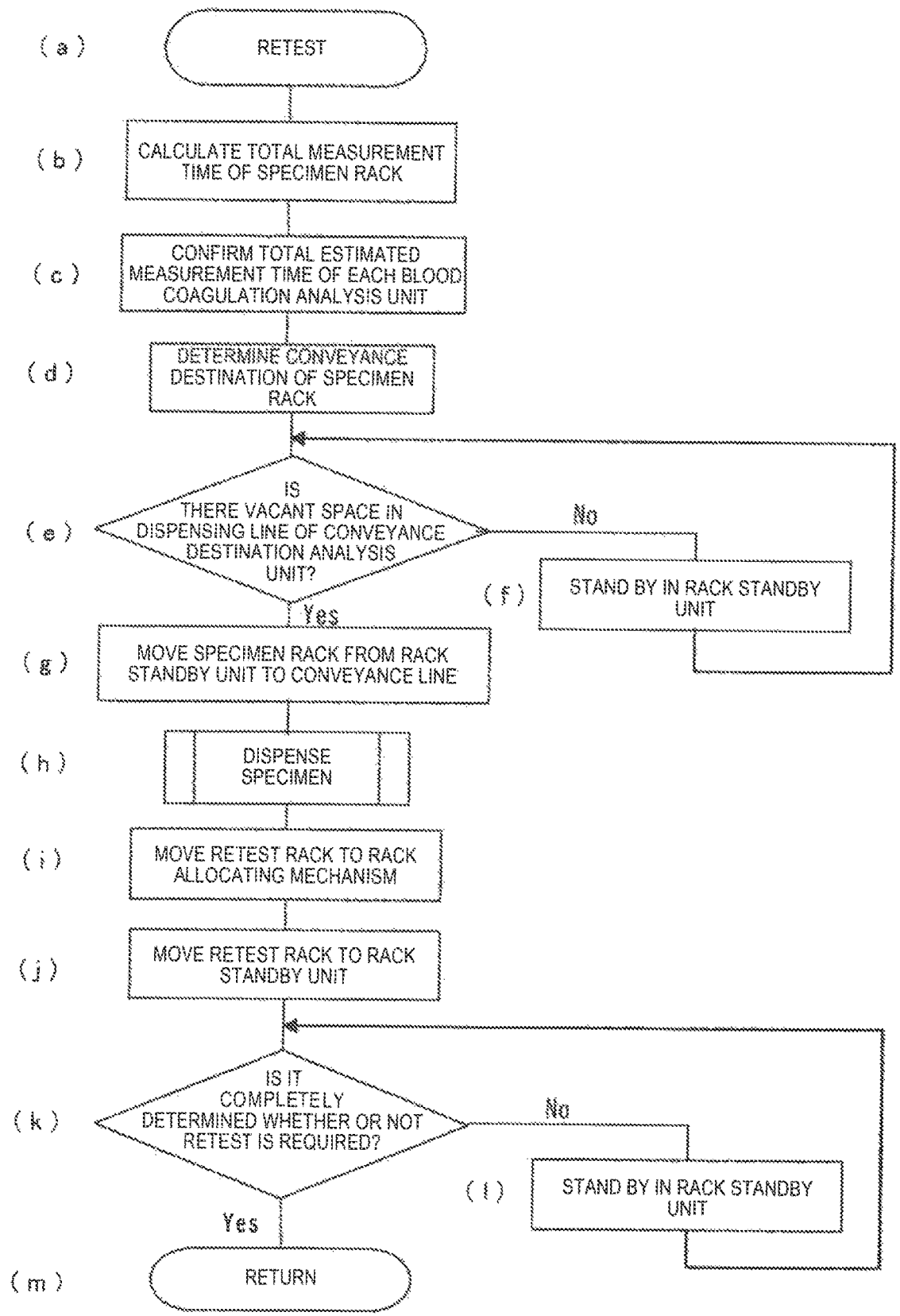

[Fig. 10]
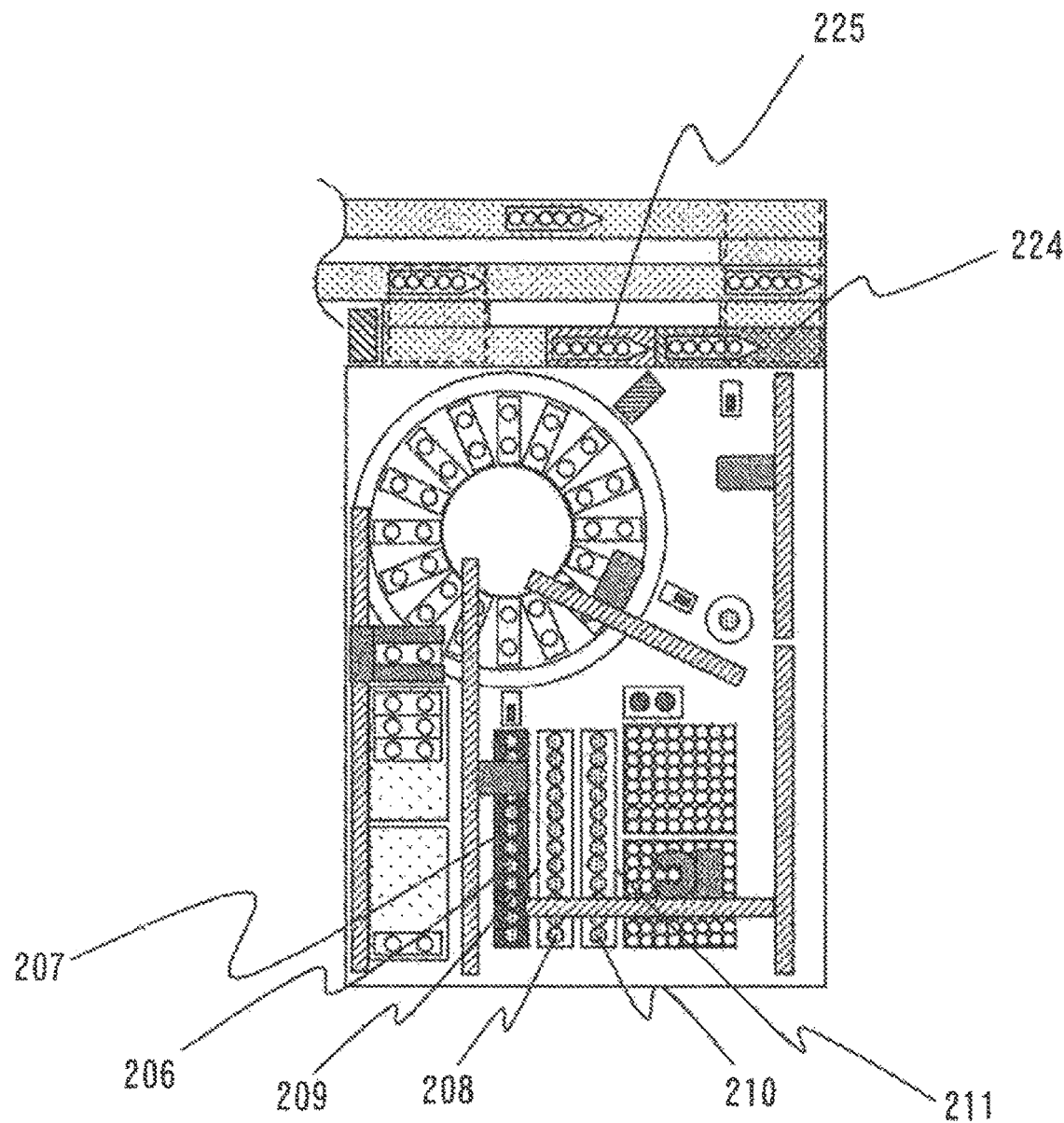

[Fig. 11]
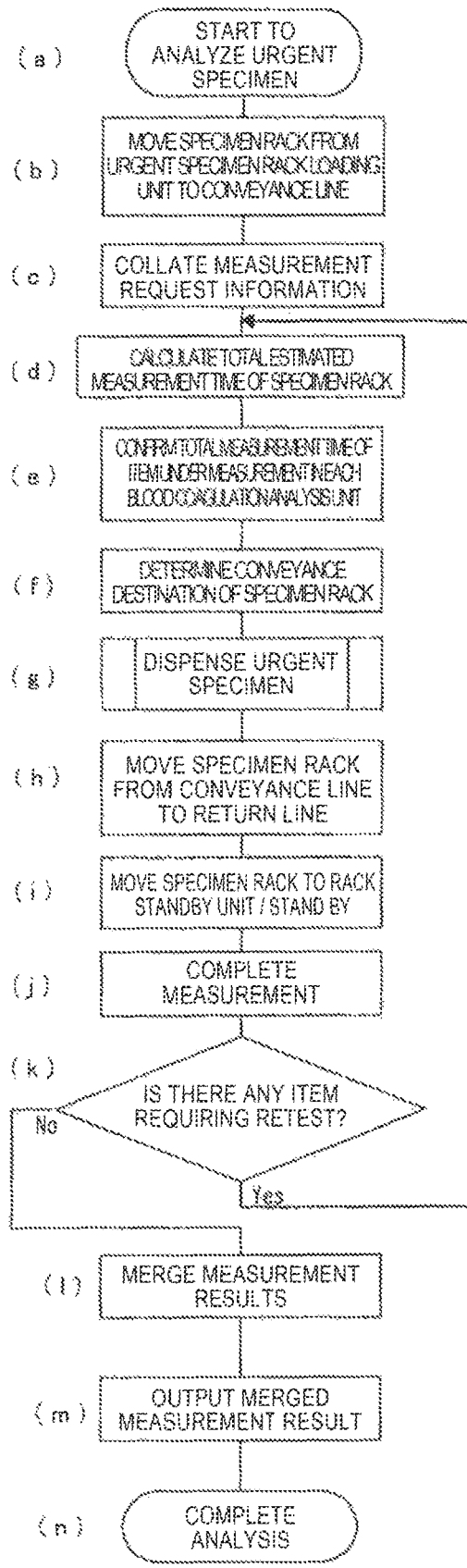

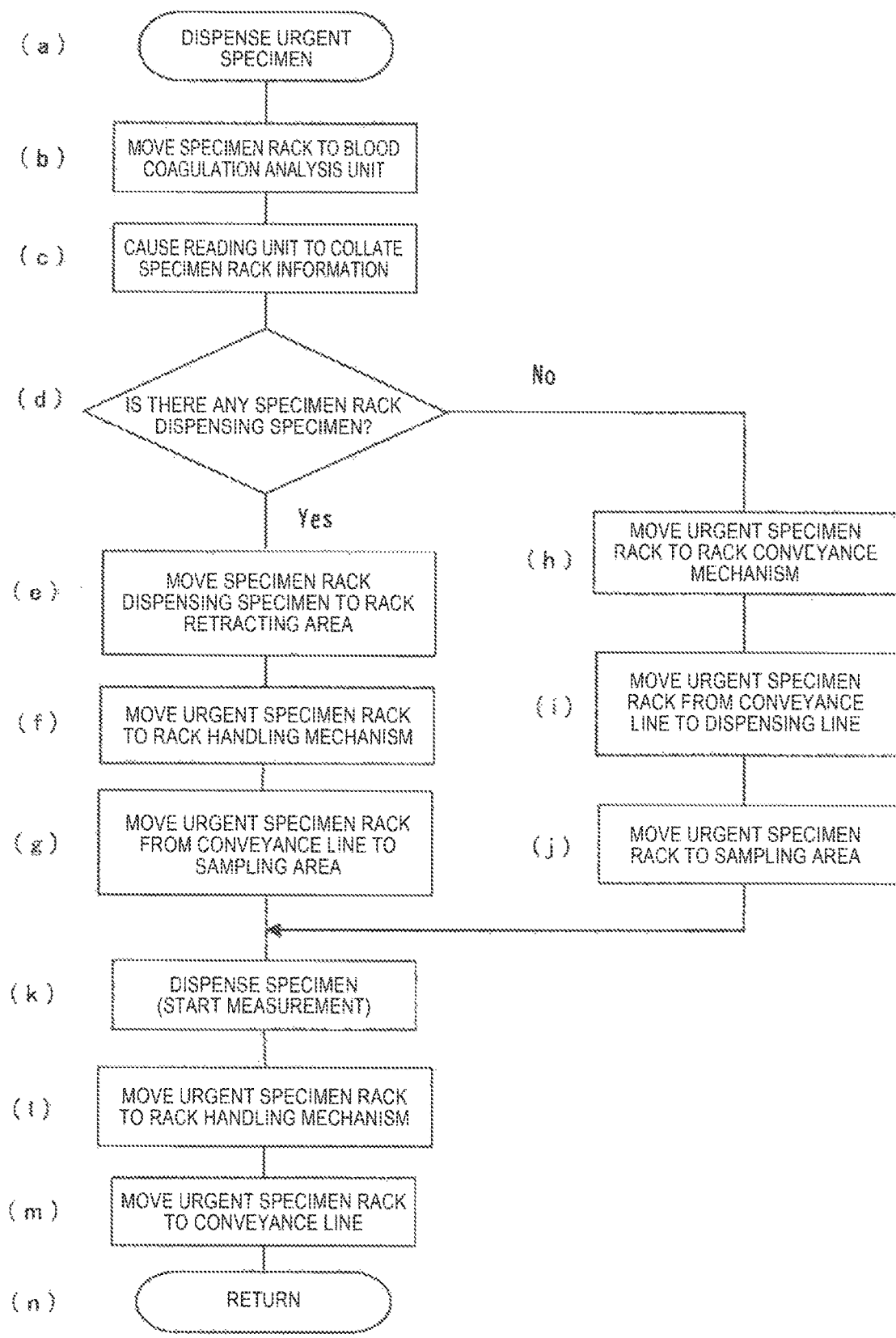

[Fig. 13]
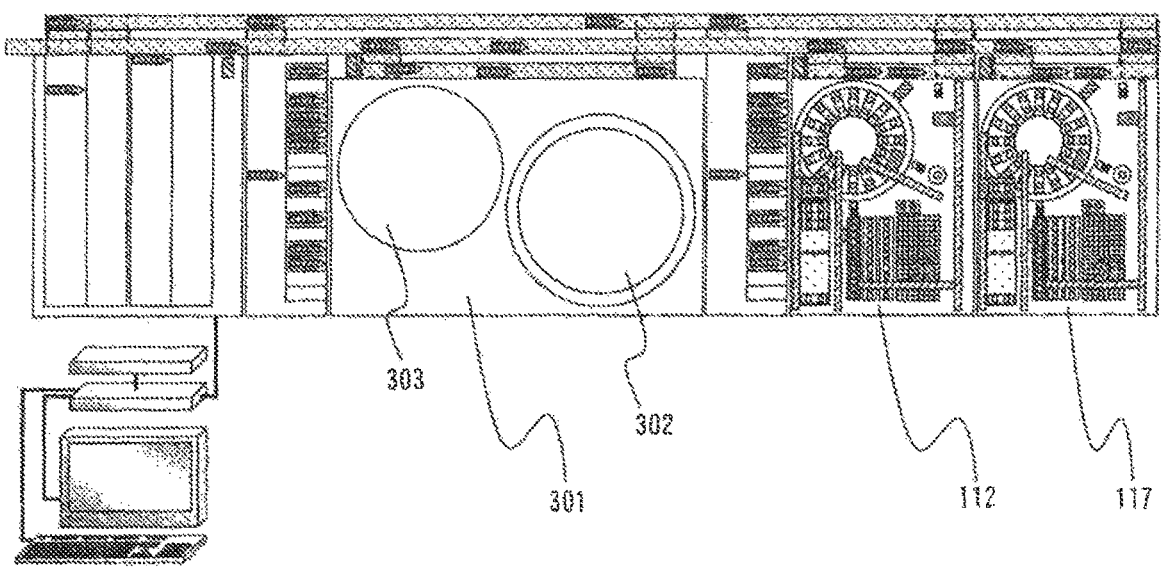

AUTOMATED ANALYZER

TECHNICAL FIELD

The present invention relates to an automated analyzer which automatically analyzes a component amount contained in a biological sample such as blood and urine, and particularly relates to an automated analyzer which enables measurement of a blood coagulation test item (hereinafter, referred to as blood coagulation analysis).

BACKGROUND ART

As a device for analyzing a target component contained in a biological sample (hereinafter, referred to as a specimen) such as blood, an automated analyzer is widely used which measures light intensity of transmitted light or scattered light having a single or a plurality of wavelengths obtained by emitting light from a light source to a reaction solution in which the specimen serving as an analysis target and a reagent are mixed with each other.

The automated analyzer includes a biochemical analysis device that performs quantitative and qualitative analysis of a target component contained in a biological specimen in the field of biochemical tests and hematology tests, and a blood coagulation analysis device that measures coagulation ability of blood serving as the specimen (hereinafter, referred to as a blood coagulation analysis device in some cases).

This coagulation ability of the blood includes exogenous ability by which the blood leaking out from the blood vessel coagulates and endogenous ability by which the blood in the blood vessel coagulates. Measurement items relating to the coagulation ability of the blood (blood coagulation time) include prothrombin time (PT) of an exogenous blood coagulation reaction test, activated partial thromboplastin time (APTT) of an endogenous blood coagulation reaction test, and a fibrinogen amount (Fbg) relating to overall blood coagulation reaction.

In the blood coagulation analysis device, in order to analyze any one of these measurement items, fibrin precipitated by adding a reagent for initiating the blood coagulation reaction is detected by using various methods including an optical method. In a case of using the optical method, the light is emitted to the reaction solution so as to detect a time-dependent light intensity change in the scattered light or the transmitted light from the fibrin precipitated in the reaction solution. In this manner, the blood coagulation time is calculated, based on a detected result. A blood coagulation time item requires photometric data at intervals of 0.1 seconds. Thus, the reaction is performed in a separate photometric port. If the reaction solution coagulates, a reaction container cannot be reused by cleaning. Consequently, the reaction container has to be discarded.

In addition to this blood coagulation time measurement, a blood coagulation/fibrinolysis test field also includes blood coagulation factor measurement and blood coagulation/fibrinolysis marker measurement. The latter coagulation/fibrinolysis marker is analyzed by a synthetic substrate method using a chromogenic synthetic substrate or by a latex agglutination method using a reagent containing latex particles in which an antibody is sensitized on (bound with) a surface. The blood coagulation time item includes PT, APTT, Fbg and the like. In addition to D-dimer or fibrin/fibrinogen degradation products (FDP), the blood coagulation/fibrinolysis marker item includes soluble fibrin monomer complex (SFMC) and plasmin-α2 plasmin inhibitor (PIC). The blood coagulation/fibrinolysis marker item is expected to increase in future, since there is a demand for early diagnosis/treatment of disseminated intravascular coagulation (DIC). Accordingly, it is desirable to achieve improved throughput or efficiency of the automated analyzer. The blood coagulation time measurement is usually completed within two to four minutes. In contrast, in a case where the coagulation ability of the blood is poor, the reaction time may be 6 minutes or longer. On the other hand, according to the synthetic substrate method and the latex agglutination method, the reaction time usually requires 10 minutes, and the reaction time is fixed similarly to the above-described biochemical analysis.

Incidentally, as the automated analyzer for clinical tests, a known device includes a stand-alone type that is operated as an independent device, and a modular type that is operated as a single device in which analysis units in a plurality of fields such as biochemical analysis and immunoassay analysis are connected to a specimen rack conveyance line in order to streamline laboratory work. The automated analyzer of the module type has a plurality of the analysis units that analyze the reaction solution in which the specimen and the reagent are mixed and reacted with each other. As a method of supplying the specimen to the analysis unit, a method is known in which a specimen rack accommodating a specimen container is conveyed via the conveyance line so as to be located at a specimen dispensing position of the analysis unit.

Since the plurality of analysis units are modularized and integrated with each other, advantageous effects can be expected in that a specimen management flow is improved and device management is streamlined. Therefore, various techniques have been devised in order to efficiently perform the measurement.

PTL 1 introduces a technique as follows. A conveyance order of specimen containers is variable by being associated with the throughput of each analysis unit, thereby obtaining an average analysis processing time in each analysis unit. In this manner, the analysis processing time is shortened as a system.

PTL 2 discloses a technique as follows. Based on analysis item information, a conveyance destination of a specimen rack is determined from the plurality of analysis units. The specimen rack is conveyed to the analysis unit which can quickly accept the specimen rack from the plurality of analysis units to which the same analysis item is assigned. In this manner, the analysis item is efficiently analyzed.

PTL 3 discloses a specimen processing system as follows. Based on each requested measurement item, an analysis unit having fewest measurement reservations is determined as the conveyance destination of the specimen rack.

CITATION LIST

Patent Literature

PTL 1: JP-A-7-92171
PTL 2: JP-A-10-339734
PTL 3: JP-A-2010-133917

SUMMARY OF INVENTION

Technical Problem

Each of PTLS 1 to 3 relates to a technique for efficiently processing the specimen in a specimen conveyance system having the module type connected thereto or the plurality of analysis devices connected thereto. According to these techniques, the specimen can be efficiently processed in a case where a biochemical item whose reaction time is determined in advance is analyzed, or in a case where the plurality of analysis units capable of measuring immune items are connected to each other.

Here, as described above, with regard to the blood coagulation time measurement, the reaction time depends on the blood coagulation ability of the specimen, and is not fixed. In a case where a plurality of blood coagulation analysis units which can measure the blood coagulation time item whose reaction time differs depending on the specimen in this way are incorporated in the module type device, there may be discrepancies between the analysis units in the specimen processing, the number of measurement times, or the measurement time. Consequently, it is considered that the entire throughput of the device becomes poor. In addition, some reagents of the blood coagulation time item are derived from living bodies. Accordingly, the expiration date of the reagents is as short as one week. If there is the discrepancy between the analysis units in the number of measurement times, the reagent may not be used within the expiration date in some cases. Therefore, the reagent is unnecessarily wasted.

However, any one of the configurations described in PTLS 1 to 3 does not consider a technique of incorporating the blood coagulation analysis units which measure the items whose reaction time differs depending on each specimen as in the blood coagulation time item. Therefore, there is a possibility that the entire throughput of the above-described device may become poor and the reagent may be unnecessarily wasted.

An object of the present invention is to realize highly efficient analysis in which the entire throughput of the device is satisfactorily maintained and unnecessary waste of the reagent is minimized, even in a module type configuration having the plurality of blood coagulation analysis units which measure the blood coagulation time items whose reaction time differs depending on each specimen.

Solution to Problem

According to an aspect of the present invention, in order to solve the above-described problem, there are provided an automated analyzer and an analysis method of an automated analyzer including a conveyance line that conveys a specimen rack accommodating a specimen container holding a specimen, a dispensing line that is disposed along the conveyance line, and that is capable of causing a plurality of the specimen racks which await specimen dispensing to stand by, a plurality of blood coagulation analysis units that are capable of analyzing blood coagulation time items whose reaction times between the specimen dispensed on the dispensing line and a reagent are different from each other depending on the specimen, a reading unit that reads analysis request information relating to the specimen, and a control unit that controls an operation for conveying the specimen rack, based on the read information. The control unit calculates a sum of estimated measurement times of measurement items requested for the specimen under analysis and the specimen on standby in each of the plurality of blood coagulation analysis units, and determines a conveyance destination of the specimen rack, based on the calculated sum of the estimated measurement times.

Advantageous Effects of Invention

According to the above-described aspect, it is possible to realize highly efficient analysis in which the entire throughput of the device is satisfactorily maintained and unnecessary waste of the reagent is minimized by the averaged and more efficient specimen processing, even in a module type configuration having the plurality of blood coagulation analysis units which measure the blood coagulation time items whose reaction time differs depending on each specimen.

BRIEF DESCRIPTION OF DRAWINGS

FIG. 1 is a view illustrating a basic configuration of an automated analyzer including blood coagulation analysis units in two modules according to the present embodiment.

FIG. 2 is a view illustrating a basic configuration of the blood coagulation analysis unit according to the present embodiment.

FIG. 3 is a view illustrating a calculation example of an estimated measurement time of a specimen rack according to the present embodiment.

FIG. 4 is a view illustrating an example of a conveyance route of the specimen rack from a rack supply unit according to the present embodiment.

FIG. 5 is a view illustrating an example of a conveyance route of the specimen rack from a rack standby unit according to the present embodiment.

FIG. 6 is a flowchart illustrating an analysis operation according to the present embodiment.

FIG. 7 is a flowchart illustrating a specimen dispensing operation of an analysis unit according to the present embodiment.

FIG. 8 is a flowchart illustrating a rack standby operation in the rack standby unit according to the present embodiment.

FIG. 9 is a flowchart illustrating a system operation of a retest according to the present embodiment.

FIG. 10 is a view illustrating a basic configuration of a sampling area and a rack retracting area on a dispensing line of the blood coagulation analysis unit according to the present embodiment.

FIG. 11 is a flowchart illustrating an analysis system operation of an urgent specimen according to the present embodiment.

FIG. 12 is a flowchart illustrating an urgent specimen dispensing operation of the analysis unit according to the present embodiment.

FIG. 13 is a view illustrating a basic configuration of the automated analyzer including a plurality of blood coagulation analysis units and a biochemical analysis unit according to the present embodiment.

DESCRIPTION OF EMBODIMENTS

Hereinafter, embodiments of the present invention will be described in detail with reference to the drawings. Throughout the description, in principle, the same reference numerals will be given to respective configuration elements having the same function in the respective drawings for describing the present embodiment, and description thereof may be omitted in some cases.

In addition, in the following description, a synthetic substrate item or a latex item in a blood coagulation test item may be referred to as a first test item, and a blood coagulation time item may be referred to as a second test item. In addition, a biochemical measurement item may be referred to as a third test item.

An example of the first test item includes D-dimer, FDP, SFMC, and PIC. An example of the second test item includes PT, APTT, and Fbg. An example of the third test item includes alanine aminotransferase (ALT) and aspartate aminotransferase (AST).

First Embodiment

<Overall Configuration of Device>

FIG. 1 is a view illustrating a basic configuration of an automated analyzer including blood coagulation analysis units in two modules according to the present embodiment.

As illustrated in the drawing, an automated analyzer 100 of a module type has a first blood coagulation analysis unit 112 and a second blood coagulation analysis unit 117 which are a plurality of analysis units for analyzing a reaction solution serving as a mixed solution of a sample and a reagent, and includes a conveyance line 104 and a return line 105 which convey a specimen rack 101 on which a specimen container accommodating a specimen is mounted in order to supply the specimen to each analysis unit. As examples of configuration elements of a conveyance system for conveying the specimen rack 101 on which the specimen container containing the specimen such as plasma serving as an analysis target, the drawing illustrates the conveyance line 104 and the return line 105 which convey the specimen rack 101 to each analysis unit, a rack supply unit 102 that supplies the specimen rack 101 onto the conveyance line 104, a rack accommodation unit 103 that accommodates the specimen rack 101 which completes analysis and reaches the rack accommodation unit 103 after moving on the return line 105, a rack standby unit 106 that causes the specimen rack awaiting specimen dispensing to stand by, a rack handling mechanism 107 that transfers the specimen rack 101 between the conveyance line 104, the return line 105, and the rack standby unit 106, and inside the rack standby unit 106, a rack allocating mechanism 109 that allocates a destination of the rack on the return line 105, based on information of the specimen rack 101, a rack returning mechanism 108 that moves the allocated specimen rack 101 to the rack accommodation unit 103, an urgent specimen rack loading unit 110 that loads the specimen rack 101 which needs urgent analysis, and a reading unit (conveyance line) 111 that reads information such as a bar code attached to the specimen rack 101 on the conveyance line 104.

The conveyance system of the first blood coagulation analysis unit 112 disposed along the conveyance line 104 includes a reading unit (first blood coagulation analysis unit) 116 for collating analysis request information relating to the specimen accommodated in the specimen rack 101 from the conveyance line 104, a first rack conveyance mechanism 114 that receives the specimen rack 101 from the conveyance line 104, a first dispensing line 113 that includes a sampling area where the specimen is dispensed, and that can await the specimen rack 101 until the specimen starts to be dispensed, and a first rack handling mechanism 115 that conveys the specimen rack 101 to the conveyance line 104 or the return line 105 after the specimen rack 101 dispenses the specimen. Here, the first dispensing line 113 includes a specimen rack conveyance mechanism that can move the specimen rack 101 in both directions of a direction the same as and a direction opposite to a traveling direction of the specimen rack 101.

Similarly to the configuration of the conveyance system of the first blood coagulation analysis unit 112, the conveyance system of the second blood coagulation analysis unit 117 disposed along the conveyance line 104 includes a reading unit (second blood coagulation analysis unit) 121 for collating analysis request information relating to the specimen accommodated in the specimen rack 101 from the conveyance line 104, a second rack conveyance mechanism 119 that receives the specimen rack 101 from the conveyance line 104, a second dispensing line 118 that includes a sampling area where the specimen is dispensed, and that can await the specimen rack 101 until the specimen starts to be dispensed, and a second rack handling mechanism 120 that conveys the specimen rack 101 to the return line 105 after the specimen is dispensed. The second dispensing line 118 includes a specimen rack conveyance mechanism that can move the specimen rack 101 in both directions of the direction the same as and the direction opposite to the traveling direction of the specimen rack 101.

Here, the conveyance of the specimen rack is not limited to the above-described method of the conveyance line 104. As long as the rack can be moved, the conveyance is applicable to any method such as a belt conveyor method and an extruding arm method of extruding and transferring a rear end portion of the rack.

Throughout all operations, the control unit 122 performs control on the operation of various configurations configuring the automated analyzer and condition settings, such as the above-described conveying operation of the specimen rack 101, the dispensing operation of the specimen and the reagent, the allocation of the specimen rack 101 based on the read information, the operation of loading and unloading, and the data processing operations including the calculation of the blood coagulation time and the concentration of the target component based on the detection result. In addition, the control unit 122 is connected to an input unit 125 such as a keyboard to which various data items relating to the analysis condition and the instructions from the operator are input, a storage unit 123 which stores input information, information read from the sample or the reagent, and information relating to the detection result, and a display unit 124 which displays the detection result and a graphical user interface (GUI) relating to various operations of the automated analyzer. In the drawing, the control unit 122 is connected to each configuration unit so as to control the overall automated analyzer. However, a configuration can be adopted so that each configuration unit includes each independent control unit.

Next, a configuration of the blood coagulation analysis unit described above with reference to FIG. 2 will be described in more detail. FIG. 2 is a view illustrating a basic configuration of the blood coagulation analysis unit according to the present embodiment. In the drawing, the blood coagulation analysis unit includes a specimen dispensing mechanism 217 that dispenses the specimen accommodated inside the specimen container on the specimen rack 101 to a reaction container 201 used for the measurement, a specimen dispensing port 216 in which the reaction container 201 serving as a target of the specimen dispensing operation can be disposed and which has a vortex stirring function for causing the first reagent dispensing mechanism 219 to dispense a diluent or a pretreatment solution, a standby block 211 that includes a plurality of standby ports 210 in which the reaction container 201 in a standby state can be disposed, and that does not have a temperature adjustment function, a reaction container magazine 202 in which a plurality of the reaction containers 201 are stocked, a reaction container transfer mechanism 212 that transfers the reaction container 201, and that loads and unloads the reaction container 201 at each position if necessary, a preheat block 209 that includes a plurality of preheat ports 208 whose temperature is adjusted to 37° C. and which raise the temperature of the specimen or a pretreatment specimen subjected to dilution processing immediately before the blood coagulation time is measured, a detection block 207 that includes a plurality of detection ports 206 whose temperature is similarly adjusted to 37° C. and which measure the blood coagulation time, a reagent disc 204 in which reagent cassettes 203 internally equipped with a reagent bottle hermetically filled with the reagent are circumferentially arranged and whose temperature is adjusted to approximately 10° C., a reagent cassette transfer mechanism. 215 that transfers the reagent cassettes 203 arranged in a reagent cassette supply unit 213 to the reagent disc 204, a reagent information reading unit 205 that reads reagent information from a medium such as a barcode and an RFID to which the measurement item of the reagent cassette 203 transferred to the reagent disc 204 and the expiration date are input, a reagent cassette accommodation unit 214 that is withdrawn from the reagent disc 204 by a reagent cassette transfer mechanism 215, and that accommodates the used reagent cassette 203, a reaction container disposal unit 223 that discards the used reaction container 201, a specimen probe washing tank 218 that washes a specimen probe, a first reagent probe washing tank 220 that washes a reagent probe of the first reagent dispensing mechanism 219, and a second reagent probe washing tank 222 that washes the reagent probe of a second reagent dispensing mechanism 221.

Here, although not illustrated in the drawing, each of the detection ports 206 in the detection block 207 includes an optical system having a light source that emits light to the reaction solution serving as a mixed solution of the specimen and the reagent which are accommodated in the reaction container 201, and a light receiving unit (detector) that detects scattered light or transmitted light of the light emitted from the light source.

The measurement of the blood coagulation time is obtained through calculation in the control unit 122, based on data of the detected light.

The first blood coagulation analysis unit 112 and the second blood coagulation analysis unit 117 can perform analysis of at least the second test item.

Figure 3:
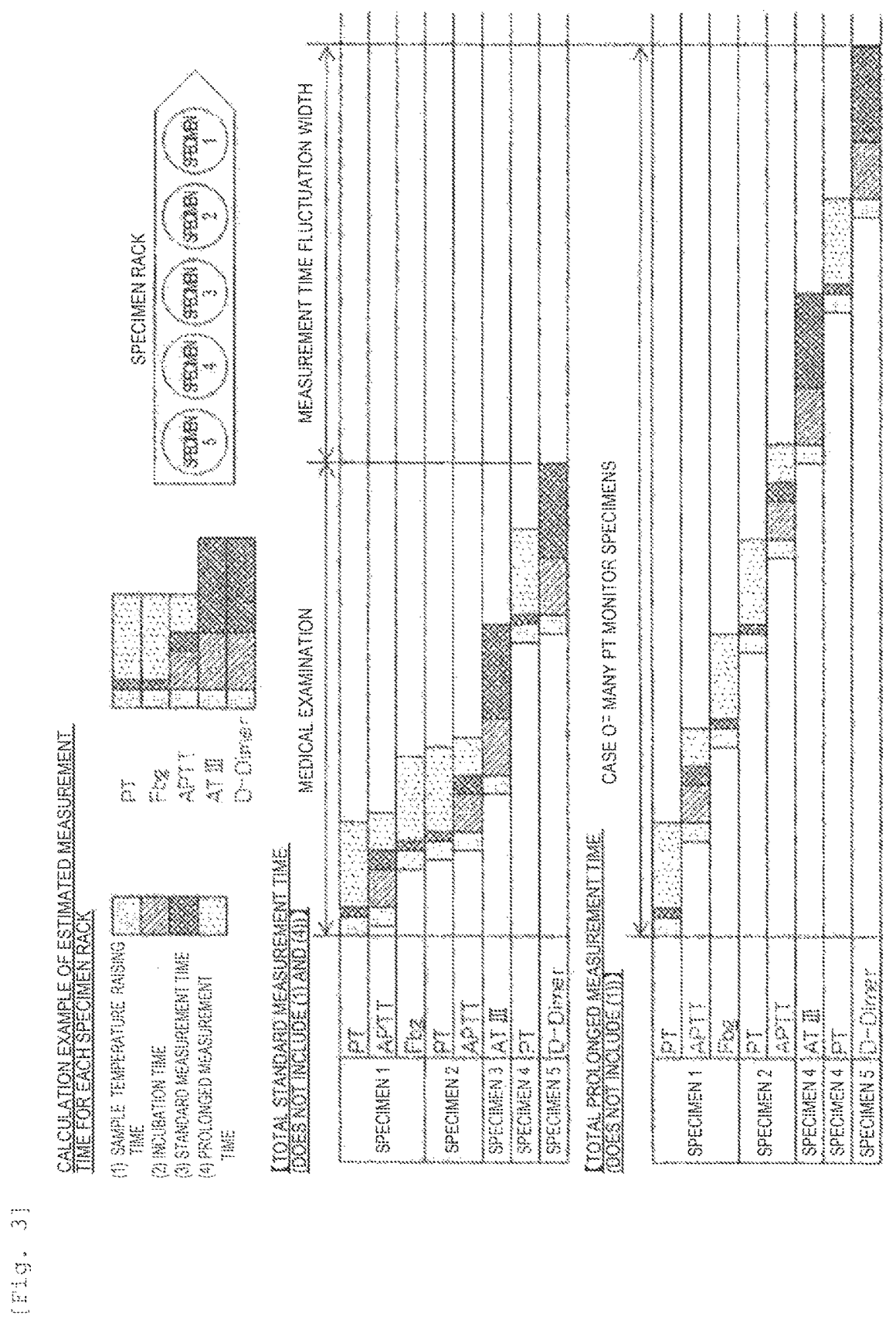

FIG. 3 is a view illustrating a calculation example of the estimated measurement time of the specimen rack according to the present embodiment. The time required for the blood coagulation measurement is classified into four categories: (1) specimen temperature raising time, (2) incubation time, (3) standard measurement time, and (4) prolonged measurement time, and are used in calculating the estimated measurement time. (1) Since the temperature is raised beforehand in the preheat block 209, the specimen temperature raising time does not need to be added to the measurement time in the detection block 207. Accordingly, the specimen temperature raising time cannot be included therein. (2) The incubation time is a fixed time determined for each measurement item required for incubation after a pretreatment solution is added to the specimen. (3) The standard measurement time may be optionally determined from a clinical point of view (time is fixed), or may be automatically determined, based on a mean value of the past measurement results (in this case, the time may fluctuates). (4) The prolonged measurement time is the time fluctuating depending on each specimen. An example is illustrated in which the time required for the blood coagulation measurement of PT, APTT, Fbg, ATIII, and D-Dimer as a representative measurement item is classified into the above-described four times.

If it is requested to analyze each of these items for a specimen 1 to a specimen 5 mounted on the specimen rack 101 by using the content illustrated in the drawing, it is possible to obtain the total standard measurement time calculated based on (2) the incubation time and (3) the standard measurement time, and the total prolonged measurement time calculated based on (2) the incubation time, (3) the standard measurement time, and (4) the prolonged measurement time. When the total standard measurement time is calculated, (3) the standard measurement time can be automatically determined from the mean value calculated based on the past measurement result for each item which is stored in the storage unit 123. According to this configuration, it is possible to set the estimated measurement time which is optimized corresponding to facilities using the automated analyzer. Therefore, it is possible to improve the accuracy of the estimated measurement time.

In addition, (3) the standard measurement time of each specimen can be determined, based on the past measurement result of a patient which is identified by patient ID information of each specimen stored in the storage unit 123. As a method of determining (3) the standard measurement time from the patient ID information, it is conceivable to employ a method of using a mean value of all of the past measurement results, a mean value of a plurality of the latest measurement result, or the latest measurement result as it is. Furthermore, depending on a measurement purpose, it is conceivable to switching (3) the standard measurement time. For example, in a case of PT measurement for monitoring an anticoagulant effect such as warfarin in treatment of thrombosis, the blood coagulation time is prolonged compared to the usual case. Accordingly, the accuracy of the estimated measurement time can be improved by switching the method to a mode for setting the standard measurement time which is prolonged as much as a predetermined time compared to the normal measurement.

In addition, in a case where a high possibility of the above-described thrombosis is determined using background information (hospital or ward in charge) of the patient which is identified by the patient ID information of each specimen, the mode can be switched so as to set the standard measurement time which is similarly prolonged as much as the predetermined time compared to the normal measurement. Alternatively, the mode can be conversely switched so as to shorten and set the standard measurement time as much as the predetermined time.

Thus, the estimated measurement time (total measurement time) in each blood coagulation analysis unit is calculated, based on the total standard measurement time calculated for each specimen rack 101 in this way. The control unit 122 controls the conveying operation so as to convey the specimen rack 101 to the analysis unit having the shortest total estimated measurement time.

Here, with regard to each of the first blood coagulation analysis unit 112 and the second blood coagulation analysis unit 117, each time the measurement of the specimen is completed in the specimen rack 101, the control unit 122 can subtract the sum of the estimated measurement times, based on the measurement time required for the actual measurement, and each time new specimen rack 101 is supplied, the control unit 122 can add the sum of the estimated measurement times, based on the measurement item requested for each specimen in the supplied specimen rack 101.

In addition, the estimated measurement completion time of each specimen or each specimen rack acquired based on the calculated estimated measurement time is displayed on the display unit 124, thereby enabling an operator to recognize the time required until the measurement is completed.

In this case, if the estimated measurement time is displayed with a width in view of a measurement time fluctuation width which is a difference between the total prolonged measurement time and the total standard measurement time, the measurement completion time can be properly delivered to the operator.

Under the control of the conveying operation of the control unit 122 based on the total measurement time calculated by the above-described method, the specimen rack 101 is conveyed to the analysis unit having the short total measurement time via a conveyance route from the rack supply unit 102 as illustrated in FIG. 4 or a conveyance route from the rack standby unit as illustrated in FIG. 5.

Here, FIG. 4 is a view illustrating an example of a conveyance route of the specimen rack from the rack supply unit according to the present embodiment. As illustrated in the drawing, the specimen rack 101 transferred from the rack supply unit 102 onto the conveyance line 104 is conveyed to the second dispensing line 118 of the second blood coagulation analysis unit 117 via the conveyance line 104 by the second rack conveyance mechanism 119.

In addition, FIG. 5 is a view illustrating an example of a conveyance route of the specimen rack from the rack standby unit according to the present embodiment. As illustrated in the drawing, the specimen rack 101 conveyed by the standby unit handling mechanism 107 from the rack standby unit 106 and transferred onto the conveyance line 104 is conveyed to the second dispensing line 118 of the second blood coagulation analysis unit 117 via the conveyance line 104 by the second rack conveyance mechanism 119.

FIG. 6 is a flowchart illustrating an analysis operation according to the present embodiment. If the analysis is requested by the input unit 125 (FIG. 6a), the control unit 122 moves the specimen rack 101 arrayed in the rack supply unit 102 to the conveyance line 104 (FIG. 6b). Thereafter, the control unit 122 causes the reading unit (the conveyance line) 111 to read an identification medium such as a barcode label affixed to the specimen rack 101 and the specimen container accommodated in the specimen rack 101. In this manner, the specimen rack number and the specimen container number are identified. The specimen rack number and the specimen container number which are identified by the reading unit (conveyance line) 111 are transmitted to the control unit 122, and the control unit 122 collates measurement request information instructed from the input unit 125 in advance by associating a type of the specimen rack 101 or a type of the analysis item instructed to each the specimen container with the specimen reception number (FIG. 6c). The collation result is stored in the storage unit 123, and is used for the subsequent process of the specimen rack 101. The control unit 122 calculates the total estimated measurement times of all of the specimen racks 101 (FIG. 6d). Thereafter, the control unit 122 confirms the total measurement time of the respective blood coagulation analysis units (FIG. 6e), and the conveyance destination of the specimen rack 101 is determined by the control unit 122 (FIG. 6f). Here, in FIG. 6e, the blood coagulation analysis unit having the smallest the total estimated measurement time calculated for each of the blood coagulation analysis units is determined as the conveyance destination of the specimen rack 101.

The control unit 122 confirms whether or not there is a vacant space in the first dispensing line 113 of the first blood coagulation analysis unit 112 or the second dispensing line 118 of the second blood coagulation analysis unit 117 (FIG. 6g). If there is the vacant space, the specimen rack 101 is conveyed to the first blood coagulation analysis unit 112 or the second blood coagulation analysis unit 117, thereby starting to dispense the specimen (FIG. 6i). On the other hand, in a case where there is no vacant space in the first dispensing line 113 or the second dispensing line 118, the control unit 122 controls the standby unit handling mechanism 107, moves the specimen rack 101 to the rack standby unit 106, and causes the specimen rack 101 to stand by (FIG. 6h).

Here, a rack standby operation (FIG. 6h) will be described in more detail with reference to FIG. 8. FIG. 8 is a flowchart illustrating the rack standby operation in the rack standby unit according to the present embodiment.

After the control unit 122 moves the specimen rack 101 to the rack standby unit 106 (FIGS. 8a to 8c), the control unit 122 frequently confirms whether or not there is the vacant space in the first dispensing line 113 of the first blood coagulation analysis unit 112 or the second dispensing line 118 of the second blood coagulation analysis unit 117 (FIG. 8d). In a case where there is no vacant space, the control unit 122 causes the specimen rack 101 to stand by in the rack standby unit 106. In a case where there is the vacant space, the control unit 122 moves the specimen rack 101 from the rack standby unit 106 to the conveyance line (FIG. 8e). That is, the specimen rack 101 stands by until there is the vacant space in the first dispensing line 113 or the second dispensing line 118.

Next, the specimen dispensing (FIG. 6i) will be described in more detail with reference to FIG. 7. FIG. 7 is a flowchart illustrating the specimen dispensing operation of the analysis unit according to the present embodiment.

The reading unit (first blood coagulation analysis unit) 116 collates specimen rack information of the specimen rack 101 (FIG. 7b) conveyed to the first blood coagulation analysis unit 112 (FIG. 7c) so as to confirm the analysis information. The control unit 122 controls the first rack conveyance mechanism 114, and moves the specimen rack 101 from the conveyance line 104 to the first dispensing line 113 (FIG. 7d). The control unit 122 conveys the specimen rack 101 to a dispensing position, and inserts a dispensing nozzle of the specimen dispensing mechanism into the specimen container where the analysis is instructed at the position. The specimen is aspirated, thereby performing control so as to dispense the specimen into the reaction container included in the first blood coagulation analysis unit 112 (FIG. 7e). In a case where two or more items are instructed to be tested for the same specimen container and in a case where the test item is instructed for the other specimen container on the same specimen rack 101, the specimen dispensing operation is continuously, similarly, and repeatedly performed.

The specimen rack 101 in which the specimen is completely dispensed for all analysis items instructed for the first blood coagulation analysis unit 112 is moved from the dispensing position to the corresponding position of the first rack handling mechanism 115 by the control unit 122. Thereafter, the control unit 122 moves the specimen rack 101 from the first dispensing line 113 to the conveyance line 104 (FIG. 7f). Alternatively, as will be described later, the control unit 122 moves the specimen rack 101 from the first dispensing line 113 to the return line 105 (FIG. 6j).

The specimen rack 101 which completely collects the specimen relating to all of the instructed analysis items is moved to the corresponding position of the first rack handling mechanism 115, and is transferred to the return line 105 by the first rack handling mechanism 115 (FIG. 6j). The control unit 122 causes the return line 105 to convey the specimen rack 101 to the rack allocating mechanism 109 (FIG. 6k). Since the specimen rack number of the specimen rack 101 conveyed to the rack allocating mechanism 109 is stored in the storage unit 123, the control unit 122 previously determines whether the specimen rack 101 does not require retest as in a control specimen rack, a standard sample rack, and cleaning solution rack, or whether the specimen rack 101 has a possibility of the retest.

If the retest is not required based on the determination, the specimen rack 101 is transferred to the rack returning mechanism 108 by the rack allocating mechanism 109 which receives a control signal of the control unit 122, and is accommodated in the rack accommodation unit 103 by the rack returning mechanism 108.

On the other hand, if there is the possibility of the retest in the specimen rack 101, the specimen rack 101 is delivered to the standby unit handling mechanism 107, and is conveyed to the rack standby unit 106. Thereafter, the specimen rack 101 stands by until it is determined whether or not the retest is required (FIG. 6*l*).

On the other hand, the specimen collected in the reaction container of each analysis unit is caused to react with the reagent dispensed by the reagent dispensing mechanism, and data corresponding to each measured analysis item is output to the control unit 122. The control unit 122 collates preset determination criteria and analysis test data. In a case where the measurement data is not suitable, information indicating that the specimen require the retest is stored in the storage unit 123 in association with the specimen rack number and the specimen container number, thereby performing the retest (FIG. 6*m*).

Here, for example, the case where the measurement data is not suitable means a case where the measurement data exceeds or falls below the preset determination criteria. The specimen rack 101 which completes the retest is transferred from the rack standby unit 106 to the return line 105 by the standby unit handling mechanism 107 (FIG. 6*n*), and is conveyed to the rack returning mechanism 108 by the return line 105. Thereafter, the specimen rack is accommodated in the rack accommodation unit 103 by the rack returning mechanism 108 (FIG. 6*o*). The first analysis test data and the retest analysis test data are merged by the control unit 122 (FIG. 6*p*), and is displayed on the display unit 124 (FIG. 6*q*), thereby completing the analysis (FIG. 6*r*).

The first dispensing line 113 includes a specimen rack conveyance mechanism capable of moving the specimen rack 101 forward and rearward in the traveling direction. In random order, the specimen dispensing mechanism 217 can have access to the specimen on the specimen rack 101. Therefore, the specimen can be retested in random order in the clogging time items whose the reaction time varies depending on the specimen. For example, if specimen containers A, B, C, D, and E are arrayed from the front in the traveling direction of the specimen rack 101, in the automated analyzer in the related art, the specimen dispensing mechanism 217 has access to the specimen containers A, B, C, D, and E in this order. However, without being limited to this order, the random order means that a sampling mechanism can have access to the specimen container in various orders such as an order of the specimen containers C, B, A, E, and D. For example, the control unit 122 can cause the specimen rack conveyance mechanism of the first dispensing line 113 to move the specimen rack 101 rearward in the direction opposite to the traveling direction. The sampling mechanism can have access to the specimen container in the order of the specimen containers C and B, or E and D. The analysis operation in the second blood coagulation analysis unit 117 is the same as that of the first blood coagulation analysis unit 112, and thus, description thereof will be omitted.

Hereinafter, control performed in a case of the retest will be described with reference to FIG. 9. FIG. 9 is a flowchart illustrating a system operation of the retest according to the present embodiment. Based on the measurement result of the first blood coagulation analysis unit 112 or the second blood coagulation analysis unit 117, in a case where the item determined to require the retest by the control unit 122 is present in the specimen of the specimen rack 101 (FIG. 9*a*), the control unit 122 calculates the total measurement time of the specimen rack 101 (FIG. 9*b*). Thereafter, the control unit 122 confirms the total measurement time of each blood coagulation analysis unit (FIG. 9*c*), and the conveyance destination of the specimen rack 101 is determined by the control unit 122 (FIG. 9*d*). Here, a conveyance destination analysis unit is selected using the total measurement time in the retest. However, the control may be performed so that the first analysis unit performs the retest.

The control unit 112 confirms whether or not there is a vacant space in the first dispensing line 113 of the first blood coagulation analysis unit 112 or the second dispensing line 118 of the second blood coagulation analysis unit 117 (FIG. 9*e*). If there is the vacant space, the specimen rack 101 is conveyed to the first blood coagulation analysis unit 112 or the second blood coagulation analysis unit 117 (FIG. 9*g*), thereby starting to dispense the specimen (FIG. 9*h*). In a case where there is no vacant space in the first dispensing line 113 or the second dispensing line 118, the specimen rack 101 stands by in the rack standby unit 106 until the dispensing line is vacant (FIG. 9*f*).

The control unit 122 causes the return line 105 to convey the specimen rack 101 which completely dispenses the specimen for retesting all items to the rack allocating mechanism 109 (FIG. 9*i*), and the specimen rack 101 is delivered to the standby unit handling mechanism 107, thereby conveying the specimen rack 101 to the rack standby unit 106 (FIG. 9*j*). The control unit 122 confirms whether or not it is determined that all of the items require the retest (FIG. 9*k*). In a case where the control unit 122 confirms that all of the items are not determined to require the retest, the specimen rack 101 stands by in the rack standby unit 106 (FIG. 9*l*).

Hereinafter, a system operation in the urgent specimen analysis according to the present embodiment will be described with reference to FIGS. 10 to 12. Here, FIG. 10 is a view illustrating a basic configuration of a sampling area and a rack retracting area on the dispensing line of the blood coagulation analysis unit according to the present embodiment. As illustrated in the drawing, the first blood coagulation analysis unit 112 or the second blood coagulation analysis unit 117 has a sampling area 224 where the specimen is dispensed on the first dispensing line 113 or the second dispensing line 118, and a rack retracting area 225 located on an upstream side of the sampling area 224 (here, the upstream side means a side close to the rack supply unit 102).

FIG. 11 is a flowchart illustrating the system operation of analyzing the urgent specimen according to the present embodiment.

If the urgent specimen analysis is requested by the input unit 125, the analysis starts. If the specimen rack 101 is installed in the urgent specimen rack loading unit 110, the specimen rack 101 in the urgent specimen rack loading unit 110 is transferred to the conveyance line 104 in preference to the specimen rack 101 present in the rack supply unit 102 (FIGS. 11a to 11b).

After the specimen rack 101 is transferred to the conveyance line 104, the reading unit (conveyance line) 111 reads an identification medium such as a barcode label affixed to the specimen rack 101 and the specimen container accommodated in the specimen rack 101, thereby identifying the specimen rack number and the specimen container number (FIG. 11c). The specimen rack number and the specimen container number which are identified by the reading unit (the conveyance line) 111 are transmitted to the control unit 122. A type of the specimen rack 101 or a type of the analysis item instructed for each specimen container is associated with the specimen reception number, and is collated with the analysis information previously instructed from the input unit 125. Based on the collation result, the conveyance destination of the specimen rack 101 is determined by the control unit 122. Here, the analysis information relating to the type of the analysis items or the conveyance destination information of the specimen rack 101 is stored in the storage unit 123, and is used for the subsequent process of the specimen rack 101.

After calculating the total measurement time of the specimen rack 101 (FIG. 11d), the control unit 122 confirms the total measurement time of the items under measurement in each blood coagulation analysis unit (FIG. 11e), and the conveyance destination of the specimen rack 101 is determined by the control unit 122 (FIG. 11f). The total measurement time of the item under measurement is calculated using the measurement time of the item under measurement on the detection port 206 and the preheat port 208. In addition, if a port for the urgent specimen is secured in the detection port 206, the preheat port 208, or the standby port 210, the urgent specimen can be more quickly analyzed.

FIG. 12 is a flowchart illustrating a dispensing operation of the urgent specimen in the analysis unit according to the present embodiment.

The specimen rack 101 is conveyed to the reading unit of the conveyance destination analysis unit, and analysis information is collated by the reading unit (FIGS. 12a to 12c). It is confirmed whether the specimen rack 101 which dispenses the specimen is present in the sampling area 224 (FIG. 12d). In a case where the specimen rack 101 is not present, the specimen rack 101 is conveyed to the corresponding position of the rack conveyance mechanism by conveyance line 104 (FIG. 12h). The specimen rack 101 stopped on the conveyance line 104 is transferred to the dispensing line by the rack conveyance mechanism (FIG. 12i), and the transferred specimen rack 101 is moved to the sampling area 224 (FIG. 12j). The dispensing nozzle of the specimen dispensing mechanism is inserted into the specimen container whose analysis is instructed, thereby dispensing the specimen to the reaction container (FIG. 12k).

In a case where the specimen rack 101 is present in the sampling area 224, the specimen rack 101 in the sampling area 224 is retracted to the rack retracting area 225 so as to cause the sampling area 224 to be vacant (FIG. 12e). The specimen rack 101 having the urgent specimen mounted thereon is conveyed to the rack handling mechanism by the conveyance line 104 (FIG. 12f), and is transferred to the sampling area 224 by the rack handling mechanism (FIG. 12g). The dispensing nozzle of the specimen dispensing mechanism is inserted into the specimen container whose analysis is instructed, thereby dispensing the specimen into the reaction container (FIG. 12k).

The specimen rack 101 under sampling and the specimen rack 101 having the urgent specimen mounted thereon may be respectively transferred. Alternatively, after the specimen rack 101 having the urgent specimen mounted thereon is transferred to the dispensing line, both the specimen racks 101 may be simultaneously moved to the dispensing line.

The specimen rack 101 which completely dispenses the specimen for all of the instructed analysis items is moved to the corresponding position of the rack handling mechanism (FIG. 12l), and is transferred to the conveyance line 104 by the rack handling mechanism (FIG. 12m). Furthermore, the specimen rack 101 is transferred to the return line 105 by the rack handling mechanism (FIG. 11h), and is conveyed to the rack allocating mechanism 109 by the return line 105.

If the retest is not required, the conveyed specimen rack 101 is transferred to the rack returning mechanism 108 by the rack allocating mechanism 109 which receives a control signal of the control unit 122, and is accommodated in the rack accommodation unit 103 by the rack returning mechanism 108. If there is a possibility of the retest in the specimen rack 101, the specimen rack 101 is delivered to the standby unit handling mechanism 107, and is conveyed to the rack standby unit 106. Thereafter, the specimen rack 101 stands by until it is determined whether or not the retest is required (FIG. 11i). The control unit 122 collates the preset determination criteria and the analysis test data. In a case where the measurement data is not suitable, the information indicating that the specimen requires the retest is associated with the specimen rack number and the specimen container number, and is stored in the storage unit 123 (FIG. 11k). The specimen rack 101 whose the retest is determined to be not required is transferred from the rack standby unit 106 to the return line 105 by the standby unit handling mechanism 107, the specimen rack 101 is conveyed to the rack returning mechanism 108 by the return line 105. Thereafter, the specimen rack 101 is accommodated in the rack accommodation unit 103 by the rack returning mechanism. 108. The first analysis test data and the retest analysis test data are displayed on the display unit 124 (FIGS. 11l to 11n).

In addition, the operation the same as the operation in the above-described urgent specimen analysis is used for all of the retests. In this manner, it is possible to shorten the time required until the test result including the retest is reported.

FIG. 13 is a view illustrating a basic configuration of the automated analyzer including a plurality of blood coagulation analysis units and a biochemical analysis unit according to the present embodiment.

A biochemical analysis unit 301 has a known configuration, and mainly includes a specimen dispensing mechanism that aspirates the specimen from the specimen rack 101, a reaction cell that discharges the aspirated specimen, a reaction disc 302 in which a plurality of reaction cells can be arranged on the circumference thereof, and which is a disk-shaped unit rotatable clockwise or counterclockwise, a reagent disc 303 which is a reagent storage for holding the reagent to be mixed with the specimen inside the reaction cell, which is a disk-shaped unit rotatable clockwise or counterclockwise, and in which a plurality of the reagent containers for accommodating the reagent can be arranged on the circumference thereof, a reagent dispensing mechanism that discharges the reagent to the reaction cell, a detector that measures the absorbance by emitting light to a mixed solution of the specimen and the reagent inside the reaction cell, an optical system having a light source, and a calculation unit that calculates predetermined component concentration included in the mixed solution, based on data obtained from the detector.

The biochemical analysis unit 301 can analyze at least a third test item. In order to suppress congestion of the specimen rack 101, it is generally desirable to dispose the biochemical analysis unit 301 having the higher specimen throughput on the upstream side of the blood coagulation analysis units 112 and 117. In addition, the reaction time of the first test item or the third test item is determined by the item different from the second test item. Accordingly, from a viewpoint that measurement scheduling is facilitated, it is desirable to dispose the biochemical analysis unit 301 on the upstream side of blood coagulation analysis units 112 and 117.

According to the present embodiment, in a case where the measurement of the first test item and the second test item is requested in the same specimen rack, the control unit determines a conveyance route of the specimen rack so that the biochemical analysis unit measures the first test item and the coagulation time analysis unit measures the second test item, and control the conveyance line. In this manner, it is possible to provide the automated analyzer which realizes the improved throughput.

In addition, in a case where the measurement of the first test item and the second test item is requested in the same specimen rack, the control unit causes the biochemical analysis unit to aspirate the specimen. Thereafter, the control unit determines a conveyance route of the specimen rack so that the blood coagulation time analysis unit aspirates the specimen, and controls the conveyance line. In this manner, it is possible to provide the automated analyzer which realizes the improved throughput. However, with regard to the arrangement of the analysis unit, the blood coagulation time analysis units 112 and 117 do not need to be arranged on the downstream side of the biochemical analysis unit 301. It is also possible to adopt a configuration in which the blood coagulation analysis units 112 and 117 are arranged on the upstream side of the biochemical analysis unit 301.

In addition, in a case where the measurement of the first test item and the second test item is requested in the same specimen rack, the control unit causes the biochemical analysis unit 301 to aspirate the specimen. Thereafter, the control unit controls the conveyance line 104 so as to convey the specimen rack to the dispensing line in a case where there is a vacant space in the first dispensing line 113 or the second dispensing line 118, and so as to convey the specimen rack 101 to the rack standby unit 106 in a case where there is no vacant space in the dispensing line. After the dispensing line is vacant, the control unit conveys the specimen rack 101 to the first dispensing line 113 or the second dispensing line 118 from the rack standby unit 106. In this manner, it is possible to provide the automated analyzer which realizes the improved throughput.

In addition, the plurality of specimen containers are mounted on the specimen rack 101, and the control unit controls the position of the specimen rack 101 in the dispensing line so as to dispense the specimen from the specimen container in the order of determining that the retest is required for the second test item in the plurality of specimen containers. In this manner, it is possible to provide the automated analyzer which realizes the improved throughput.

In addition, in a case where the measurement is requested for all of the first, second, and third test items in the same specimen rack, the control unit determines whether or not all of the second test items of the specimen rack require the retest. At this time, the control unit controls the conveyance line so as to convey the specimen rack to the second dispensing line in a case where the time at which the specimen is completely aspirated for the retest of the second test item of the specimen rack is earlier than the time required until it is determined whether or not all of the first and third test items require the retest. In this manner, it is possible to provide the automated analyzer which realizes the improved throughput.

REFERENCE SIGNS LIST

100: AUTOMATED ANALYZER
101: SPECIMEN RACK
102: RACK SUPPLY UNIT
103: RACK ACCOMMODATION UNIT
104: CONVEYANCE LINE
105: RETURN LINE
106: RACK STANDBY UNIT
107: STANDBY UNIT HANDLING MECHANISM
108: RACK RETURNING MECHANISM
109: RACK ALLOCATING MECHANISM
110: URGENT SPECIMEN RACK LOADING UNIT
111: READING UNIT (CONVEYANCE LINE)
112: FIRST BLOOD COAGULATION ANALYSIS UNIT
113: FIRST DISPENSING LINE
114: FIRST RACK CONVEYANCE MECHANISM
115: FIRST RACK HANDLING MECHANISM
116: READING UNIT (FIRST BLOOD COAGULATION ANALYSIS UNIT)
117: SECOND BLOOD COAGULATION ANALYSIS UNIT
118: SECOND DISPENSING LINE
119: SECOND RACK CONVEYANCE MECHANISM
120: SECOND RACK HANDLING MECHANISM
121: READING UNIT (SECOND BLOOD COAGULATION ANALYSIS UNIT)
122: CONTROL UNIT
123: STORAGE UNIT
124: DISPLAY UNIT
125: INPUT UNIT
201: REACTION CONTAINER
202: REACTION CONTAINER MAGAZINE
203: REAGENT CASSETTE
204: REAGENT DISC
205: REAGENT INFORMATION READING UNIT
206: DETECTION PORT
207: DETECTION BLOCK
208: PREHEAT PORT
209: PREHEAT BLOCK
210: STANDBY PORT
211: STANDBY BLOCK
212: REACTION CONTAINER TRANSFER MECHANISM
213: REAGENT CASSETTE SUPPLY UNIT
214: REAGENT CASSETTE ACCOMMODATION UNIT
215: REAGENT CASSETTE TRANSFER MECHANISM
216: SPECIMEN DISPENSING PORT
217: SPECIMEN DISPENSING MECHANISM
218: SPECIMEN PROBE WASHING TANK
219: FIRST REAGENT DISPENSING MECHANISM
220: FIRST REAGENT PROBE WASHING TANK
221: SECOND REAGENT DISPENSING MECHANISM
222: SECOND REAGENT PROBE WASHING TANK
223: REACTION CONTAINER DISPOSAL UNIT
224: SAMPLING AREA
225: RACK RETRACTING AREA
301: BIOCHEMICAL ANALYSIS UNIT
302: REACTION DISC
303: REAGENT DISC

The invention claimed is:

1. An automated analyzer comprising:
a conveyance line that conveys a specimen rack accommodating a specimen container holding a specimen;
a dispensing line that is disposed along the conveyance line, and that is capable of causing a plurality of the specimen racks which await specimen dispensing to stand by;
a plurality of blood coagulation analysis units that are capable of analyzing blood coagulation time items whose reaction times between the specimen dispensed on the dispensing line and a reagent are different from each other depending on the specimen;
a reading unit that reads analysis request information relating to the specimen; and
a control unit that controls an operation for conveying the specimen rack, based on the read information,
wherein the control unit calculates a sum of estimated measurement times of measurement items requested for the specimen under analysis and the specimen on standby in each of the plurality of blood coagulation analysis units, and determines a conveyance destination blood coagulation anlysis unit for the specimen rack containing the specimen on standby, based on the calculated sum of the estimated measurement times.

2. The automated analyzer according to claim 1,
wherein the control unit conveys the specimen rack to the blood coagulation analysis unit in which the calculated sum of the estimated measurement times is smallest among the plurality of blood coagulation analysis units.

3. The automated analyzer according to claim 2,
wherein every time that the measurement of each specimen in the specimen rack is completed by each of the plurality of blood coagulation analysis units, the control unit subtracts the sum of the estimated measurement times from a measurement time required for actual measurement, and
wherein every time that a new specimen rack is supplied, the control unit adds the measurement time of the new specimen rack to the sum of the estimated measurement times, based on the measurement item requested for each specimen in the supplied specimen rack.

4. The automated analyzer according to claim 1,
wherein the control unit calculates the sum of the estimated measurement times, based on a sum of an incubation time in each measurement item and a preset standard measurement time.

5. The automated analyzer according to claim 4,
wherein the control unit sets the standard measurement time, based on a mean value of times required for the measurement of respective measurement items measured in each of the plurality of blood coagulation analysis units.

6. The automated analyzer according to claim 4,
wherein the control unit sets the standard measurement time, based on a past measurement result of a patient identified with reference to ID information of the patient of each specimen read by the reading unit.

7. The automated analyzer according to claim 6,
wherein the control unit sets the standard measurement time, based on a mean value of times required for the measurement with reference to the past measurement result of the identified patient.

8. The automated analyzer according to claim 4,
wherein the control unit sets the standard measurement time so as to be longer or shorter than a normal measurement time, depending on a measurement purpose of the specimen.

9. The automated analyzer according to claim 1, further comprising:
a display unit,
wherein the control unit acquires an estimated measurement completion time of each specimen, based on the estimated measurement time for each specimen in the calculated sum of the estimated measurement time, and causes the display unit to display the acquired estimated measurement completion time.

10. The automated analyzer according to claim 9,
wherein the control unit calculates a fluctuation width of measurement times, based on a total estimated measurement time calculated based on a sum of an incubation time in each measurement item and a preset standard measurement time, and a total prolonged measurement time calculated based on a sum of the estimated measurement time and a prolonged measurement time which differs depending on each specimen, and causes the display unit to display the calculated fluctuation width together with the estimated measurement completion time.

11. The automated analyzer according to claim 1,
wherein when an urgent specimen is analyzed, the control unit calculates a sum of estimated measurement times of measurement items requested for the specimen under analysis in each of the plurality of blood coagulation analysis units, and conveys the specimen rack accommodating the urgent specimen, based on the calculated sum of the estimated measurement times.

12. An analysis method of an automated analyzer comprising:
conveying, using a conveyance line, a specimen rack accommodating a specimen container holding a specimen;
using a dispensing line that is disposed along the conveyance line, causing a plurality of the specimen racks which await specimen dispensing to stand by;
using a plurality of blood coagulation analysis, analyzing blood coagulation time items whose reaction times between the specimen dispensed on the dispensing line and a reagent are different from each other depending on the specimen;
reading analysis request information relating to the specimen using a reading unit; and
controlling an operation for conveying the specimen rack, based on the read information, using a control unit,
wherein the control unit calculates a sum of estimated measurement times of measurement items requested for the specimen under analysis and the specimen on standby in each the plurality of blood coagulation analysis units, and determines a conveyance destination blood coagulation analysis unit for the specimen rack containing the specimen on standby, based on the calculated sum of the estimated measurement times.

* * * * *